(12) United States Patent
Niu et al.

(10) Patent No.: US 10,345,373 B2
(45) Date of Patent: Jul. 9, 2019

(54) METHOD FOR INSPECTING SEMICONDUCTOR DEVICE STRUCTURE

(71) Applicant: Taiwan Semiconductor Manufacturing Co., Ltd., Hsinchu (TW)

(72) Inventors: Baohua Niu, Hsinchu (TW); Chia-Nan Ke, Hsinchu County (TW); Chi-Chun Lin, Hsinchu (TW)

(73) Assignee: Taiwan Semiconductor Manufacturing Co., Ltd., Hsinchu (TW)

( * ) Notice: Subject to any disclaimer, the term of this patent is extended or adjusted under 35 U.S.C. 154(b) by 116 days.

(21) Appl. No.: 15/720,839

(22) Filed: Sep. 29, 2017

(65) Prior Publication Data

US 2019/0101586 A1   Apr. 4, 2019

(51) Int. Cl.

| | |
|---|---|
| *G03F 7/20* | (2006.01) |
| *G01N 21/88* | (2006.01) |
| *G01N 21/95* | (2006.01) |
| *G01R 31/28* | (2006.01) |
| *H01L 21/66* | (2006.01) |
| *G01R 31/265* | (2006.01) |
| *G01R 31/303* | (2006.01) |

(52) U.S. Cl.
CPC ..... *G01R 31/2851* (2013.01); *G01N 21/8806* (2013.01); *G01N 21/9501* (2013.01);
(Continued)

(58) Field of Classification Search
CPC ............ G01R 31/2653; G01R 31/2656; G01R 31/2851; G01R 31/2896; G01R 31/302; G01R 31/308; G01R 31/309; G01R 31/311; G01R 31/303; G01R 31/304; H01L 22/10; H01L 22/12; G01N 21/8806; G01N 21/9501; G01N 21/956; G01N 21/95684; G01N 21/95692; G01N 2021/95638; G01N 2021/95646; G01N 2021/95653; G01N 2021/95661; G01N 2021/95669; G03F 7/7065; G06T 7/004; G06T 7/008
(Continued)

(56) References Cited

U.S. PATENT DOCUMENTS

| | | | | |
|---|---|---|---|---|
| 5,073,951 A | * | 12/1991 | Hayashi .................. | G11B 5/825 348/125 |
| 5,334,844 A | * | 8/1994 | Pollard .............. | G01N 21/8806 136/290 |

(Continued)

*Primary Examiner* — Gordon J Stock, Jr.
(74) *Attorney, Agent, or Firm* — Birch, Stewart, Kolasch & Birch, LLP

(57) ABSTRACT

A method for inspecting a semiconductor device structure is provided. The method includes receiving a semiconductor device structure having a to-be-inspected feature. The semiconductor device structure has a first surface and a second surface. The method also includes applying a polymer-containing solution over the first surface of the semiconductor device structure. The method further includes disposing a transparent substrate over the first surface of the semiconductor device structure and the polymer-containing solution. In addition, the method includes irradiating the polymer-containing solution with a light to form an adhesive layer between the transparent substrate and the semiconductor device structure. The adhesive layer bonds the transparent substrate and the semiconductor device structure. The method also includes inspecting the to-be-inspected feature.

20 Claims, 16 Drawing Sheets

(52) U.S. Cl.
CPC ..... *G01R 31/2653* (2013.01); *G01R 31/2656* (2013.01); *G01R 31/303* (2013.01); *G03F 7/7065* (2013.01); *H01L 22/12* (2013.01)

(58) Field of Classification Search
USPC .......................................... 356/237.1–237.6
See application file for complete search history.

(56) References Cited

U.S. PATENT DOCUMENTS

| | | | | |
|---|---|---|---|---|
| 5,821,549 | A | * | 10/1998 | Talbot ..................... H01L 22/12 850/62 |
| 6,331,889 | B1 | * | 12/2001 | Kaupp ................ G01N 21/9506 356/239.1 |
| 6,452,176 | B1 | * | 9/2002 | Davis .................. H01J 37/2955 250/310 |
| 9,494,409 | B2 | * | 11/2016 | Schonleber ........ G01B 11/0625 |
| 9,664,625 | B2 | * | 5/2017 | Zhou .................. G01N 21/9501 |
| 9,947,567 | B2 | * | 4/2018 | Dang ................. H01L 21/02057 |
| 10,224,229 | B2 | * | 3/2019 | Andry .................... B23K 26/57 |
| 2005/0009239 | A1 | * | 1/2005 | Wolff ................ H01L 27/14618 438/123 |
| 2006/0003483 | A1 | * | 1/2006 | Wolff ................ H01L 27/14618 438/65 |
| 2012/0202300 | A1 | * | 8/2012 | Yu .......................... H01L 22/12 438/5 |
| 2014/0103499 | A1 | * | 4/2014 | Andry ................. H01L 21/6835 257/644 |

\* cited by examiner

METHOD FOR INSPECTING SEMICONDUCTOR DEVICE STRUCTURE

BACKGROUND

The semiconductor integrated circuit (IC) industry has experienced rapid growth. Technological advances in IC materials and design have produced generations of ICs. Each generation has smaller and more complex circuits than the previous generation. In the course of IC evolution, functional density (i.e., the number of interconnected devices per chip area) has generally increased while geometric size (i.e., the smallest component (or line) that can be created using a fabrication process) has decreased. This scaling-down process generally provides benefits by increasing production efficiency and lowering associated costs.

As technology node sizes decrease and integrated circuits (ICs) become smaller, a microscopic observation of a semiconductor device structure (such as a semiconductor wafer and/or a device under test (DUT)) plays an important role for inspecting yield-limiting defects, design-functional defects and performance-limiting defects.

However, since feature sizes continue to decrease, the microscopic observation of the semiconductor device structure continues to become more difficult to perform. Therefore, it is a challenge to inspect the semiconductor device structures at smaller and smaller sizes.

BRIEF DESCRIPTION OF THE DRAWINGS

Aspects of the present disclosure are best understood from the following detailed description when read with the accompanying figures. It should be noted that, in accordance with the standard practice in the industry, various features are not drawn to scale. In fact, the dimensions of the various features may be arbitrarily increased or reduced for clarity of discussion.

DETAILED DESCRIPTION

Figure 1A:
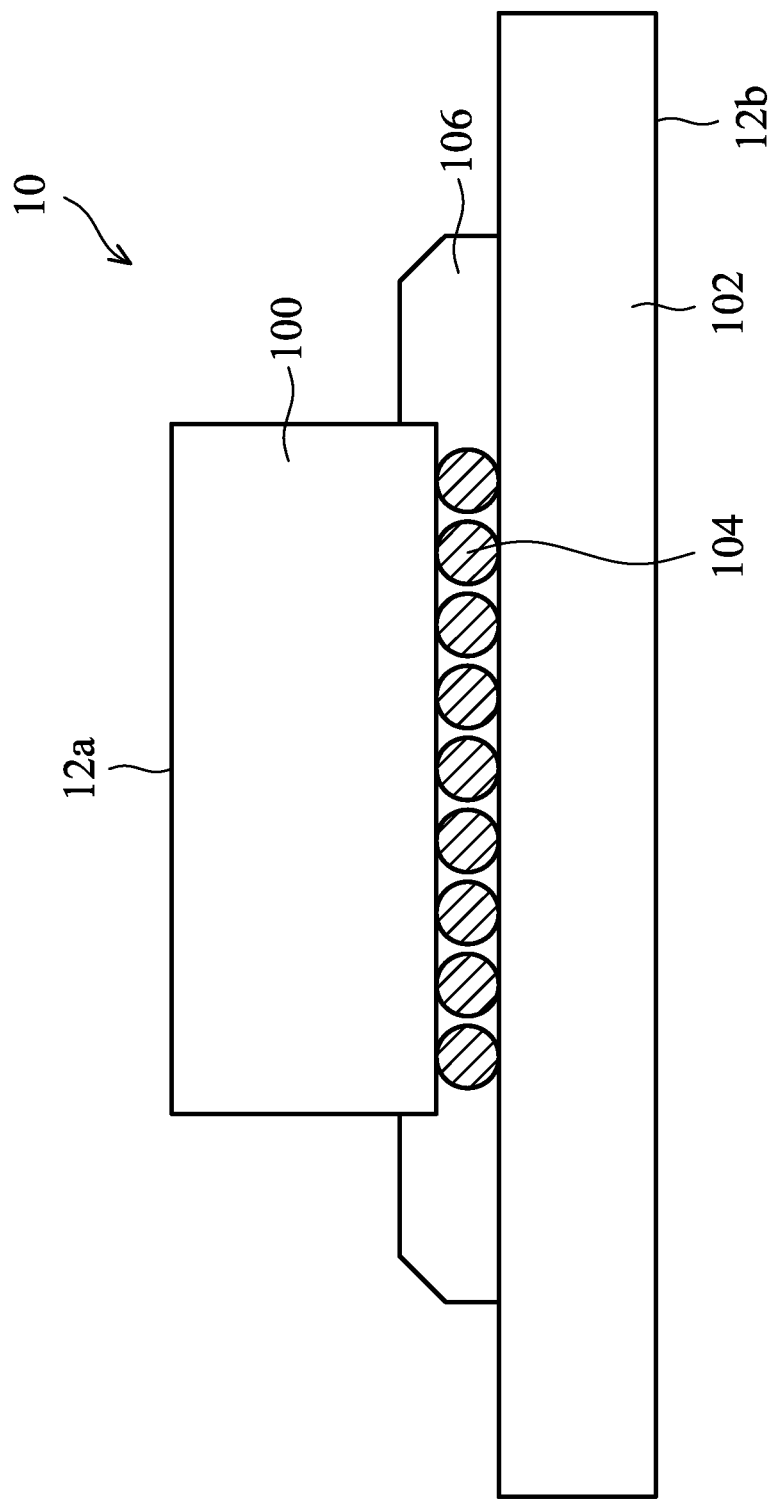
FIGS. 1A-1G are cross-sectional views of various stages of a process for inspecting a semiconductor device structure, in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Some embodiments of the disclosure are described. Additional operations can be provided before, during, and/or after the stages described in these embodiments. Some of the stages that are described can be replaced or eliminated for different embodiments. Additional features can be added to the semiconductor device structure. Some of the features described below can be replaced or eliminated for different embodiments. Although some embodiments are discussed with operations performed in a particular order, these operations may be performed in another logical order.

For yield analysis, defect localization and analysis, functional debug and performance debug on flip chip semiconductor integrated circuits, one or more inspection operations are utilized to inspect the semiconductor wafer or DUT. The inspection operations are used to instantly and quickly identify process yield-limiting defects, design-functional defects and performance-limiting defects. Therefore, the manufacturing processes may be adjusted timely to improve product yield.

FIGS. 1A-1G are cross-sectional views of various stages of a process for forming a chip package, in accordance with some embodiments. FIG. 2 is a flow chart illustrating a method 200 for inspecting a semiconductor device structure, in accordance with some embodiments. In some embodiments, the method 200 begins with an operation 202 in which a semiconductor device structure having a to-be-inspected feature is received, as shown in FIG. 2. In some embodiments, the semiconductor device structure is a chip package. As shown in FIG. 1A, a chip package 10 (that is to be inspected) is provided or received.

In some embodiments, the chip package 10 includes a semiconductor die (or semiconductor chip) 100. In some embodiments, the semiconductor die 100 includes a CMOS chip, a micro-electro-mechanical system (MEMS) chip, a nano-electro-mechanical system (NEMS) chip, or another suitable chip. The chip package 10 that is to be inspected or tested may also be called a device under test (DUT).

However, embodiments of the disclosure are not limited thereto. Many variations and/or modifications can be made to embodiments of the disclosure. In some other embodiments, the semiconductor structure that is to be inspected is a wafer-level package structure which includes one or more semiconductor wafers. The packaged semiconductor wafer may include a CMOS wafer, a micro-electro-mechanical system (MEMS) wafer, a nano-electro-mechanical system (NEMS) wafer, or another suitable wafer.

In some embodiments, the chip package 10 further includes a package substrate 102. The semiconductor die 100 may be bonded with the package substrate 102 through bonding elements 104, as shown in FIG. 1A. In some embodiments, an underfill layer 106 is formed between the semiconductor die 100 and the package substrate 102 to surround the bonding elements 104. The underfill layer 106 may prevent the bonding element 104 from being damaged or degraded by moisture. The underfill layer 106 may be made of or include an epoxy-containing resin. The underfill layer 106 may have a thickness in a range from about 50 μm to about 100 μm.

In some embodiments, the bonding elements 104 are conductive elements that include solder bumps, copper pillar bumps, other suitable conductive bumps, or a combination thereof. In some embodiments, each of the bonding elements 104 has a thickness that is in a range from about 70 μm to about 120 μm. A reflow process may be used to form the bonding elements 104 between the semiconductor die 100 and the package substrate 102.

In some embodiments, the package substrate 102 is a printed circuit board which includes a polymer-based substrate with conductive features formed thereon and therein. The package substrate 102 may have a thickness that is in a range from about 500 μm to about 2000 μm. The bonding element 104 may be bonded with conductive pads (not shown) of the package substrate 102. In some other embodiments, the package substrate 102 is a semiconductor substrate, such as a silicon substrate.

Afterwards, the method 200 continues with an operation S204 in which a target region of the semiconductor device structure is identified, as shown in FIG. 2 in accordance with some embodiments. In some embodiments, the target region contains a feature that is intended to be inspected and/or observed.

Figure 1B:
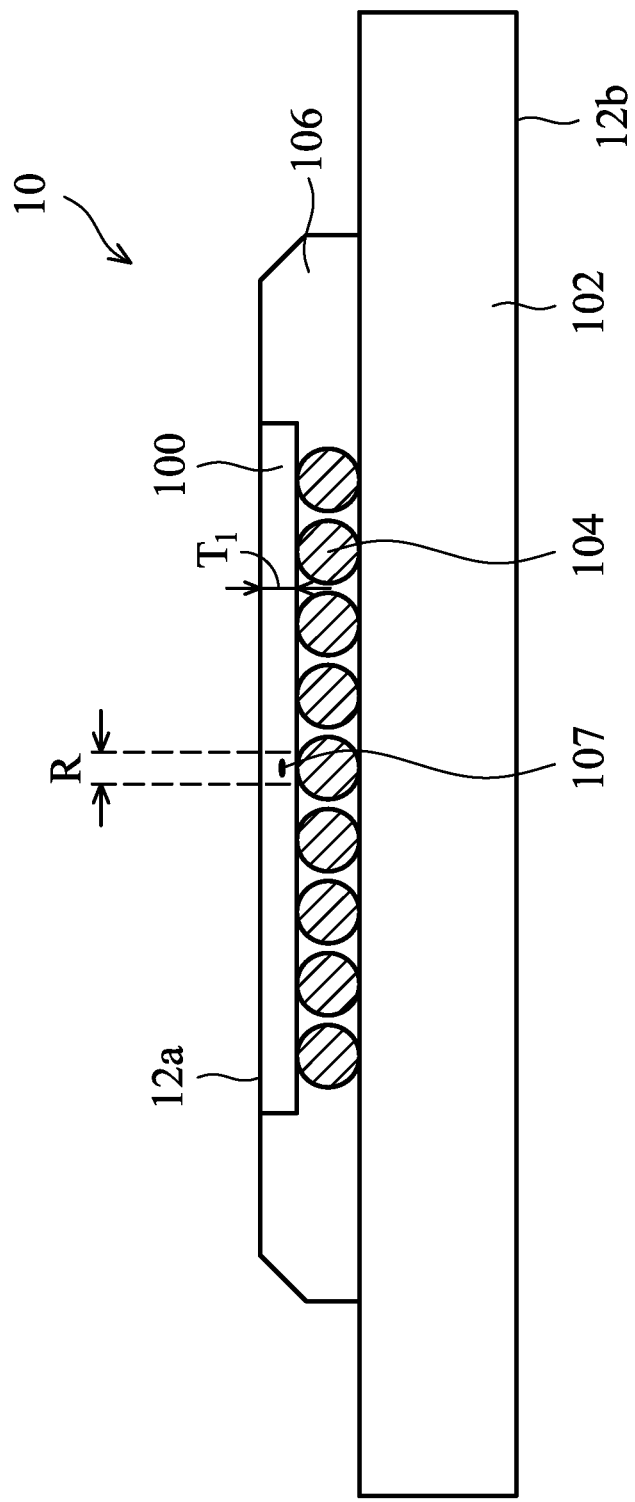
Figure 2:
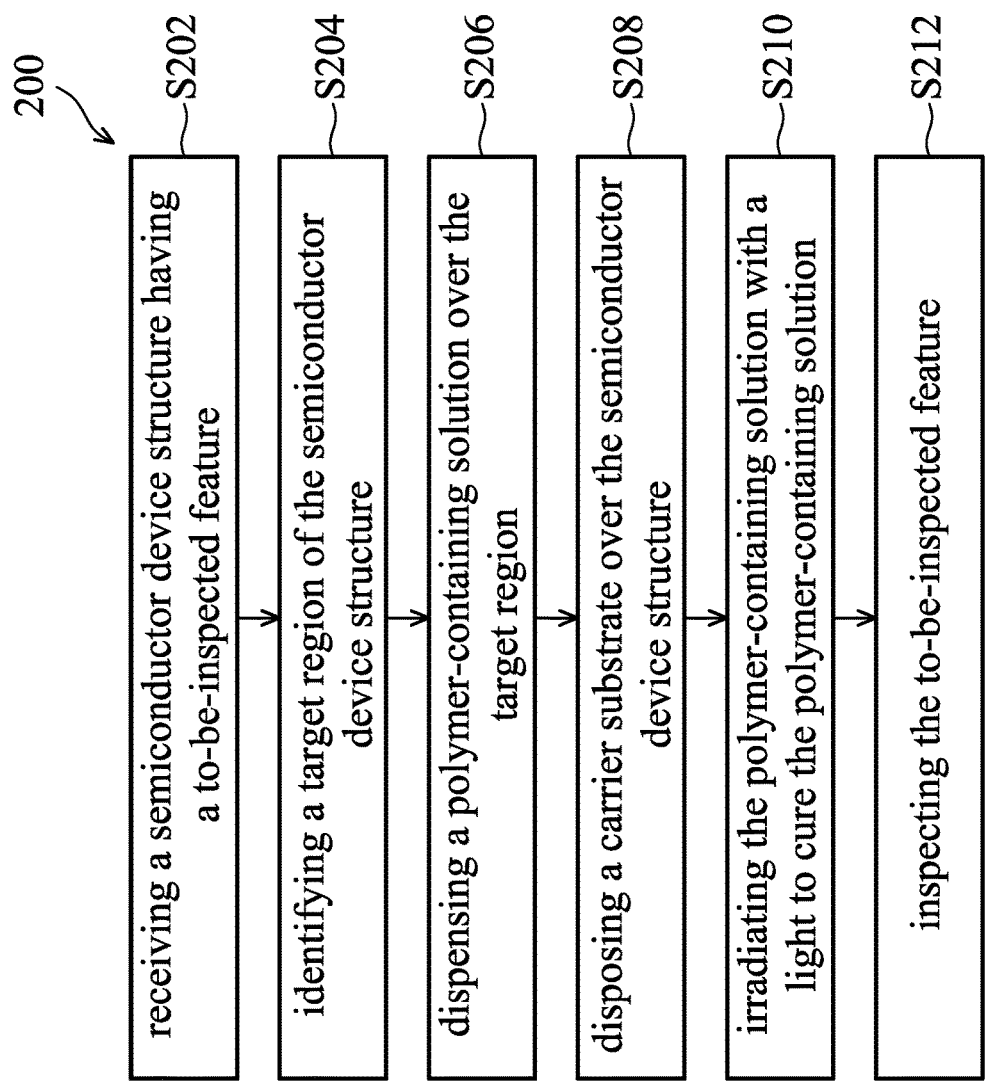
FIG. 2 is a flow chart illustrating a method for inspecting a semiconductor device structure, in accordance with some embodiments.

As shown in FIG. 1B, before the target region is identified, the chip package 10 is thinned to facilitate subsequent inspection operations of the chip package 10, in accordance with some embodiments. The target region containing the to-be-inspected feature may be identified more easily and/or more precisely after the chip package 10 is thinned.

As shown in FIG. 1B, the chip package 10 has a first surface 12a and a second surface 12b. In some embodiments, the first surface 12a is the back side surface of the semiconductor die 100. In some embodiments, the thinning of the chip package 10 is achieved by thinning the semiconductor die 100 from the surface 12a. In some embodiments, the semiconductor die 100 is thinned using a mechanical grinding process, a chemical mechanical polishing (CMP) process, an etching process, a dry polishing process, one or more other applicable processes, or a combination thereof.

The semiconductor die 100 may be thinned to have a smaller thickness $T_1$. The thickness $T_1$ may be in a range from about 100 μm to about 10 μm. In some embodiments, the semiconductor die 100 may have an original thickness of about 750 μm. After being thinned, the semiconductor die 100 may have a thickness of about 50 μm.

Since the semiconductor die 100 is thinned, it may become easier to find out the yield-limiting defects, performance-limiting defects, and/or one or more other features intended to be observed. In some embodiments, the chip package 10 is inspected to locate and/or to identify a target region R where a to-be-inspected feature 107 is positioned, as shown in FIG. 1B. The to-be-inspected feature 107 may be a yield-limiting defect or a performance-limiting defect.

In some embodiments, the target region R is identified using an optical microscope. In some embodiments, the target region R is identified using an infrared light. The infrared light may be used as a light source when inspecting the chip package 10 using the optical microscope. The infrared light may be used to roughly identify the target region R containing the to-be-inspected feature 107. The precise position and/or depth of the to-be-inspected feature 107 may be identified and/or inspected later.

In some embodiments mentioned above, the target region R is identified after the thinning of the semiconductor die 100. However, embodiments of the disclosure are not limited thereto. Many variations and/or modifications can be made to embodiments of the disclosure. In some other embodiments, the semiconductor die 100 is not thinned before the target region R is identified or located.

Figure 1C:
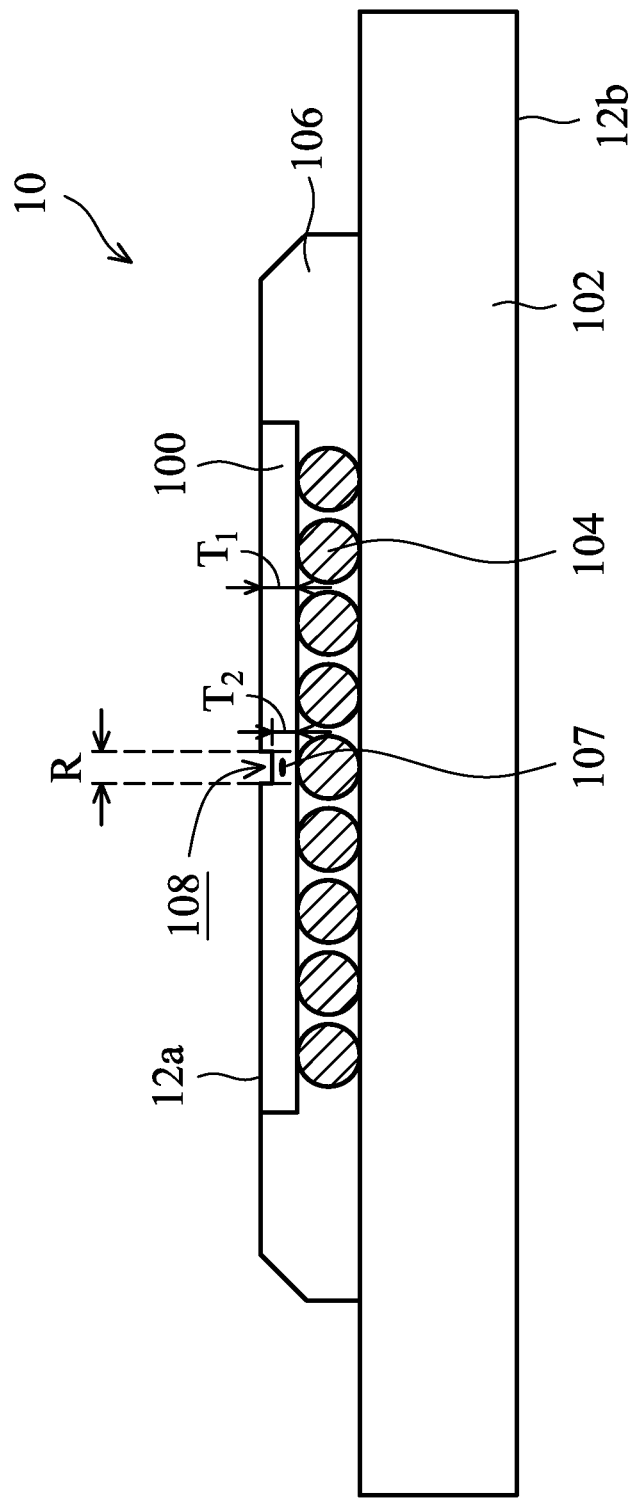

As shown in FIG. 1C, after the target region R is identified, the target region R is marked, in accordance with some embodiments. In some embodiments, the target region R is thinned or partially removed to form a mark recess 108, as shown in FIG. 1C. The mark recess 108 is used to indicate the position of the target region R.

In some embodiments, the mark recess 108 is formed using a mechanical drilling process. However, embodiments of the disclosure are not limited thereto. Many variations and/or modifications can be made to embodiments of the disclosure. In some other embodiments, the mark recess 108 is formed using a laser drilling process, an etching process, a mechanical drilling process, an ion beam drilling process, an electron beam drilling process, one or more other applicable processes, or a combination thereof.

In some embodiments, after the formation of the mark recess 108, the remaining portion of the target region R has a smaller thickness $T_2$, as shown in FIG. 1C. In some embodiments, the thickness $T_2$ is in a range from about 100 nm to about 5000 nm.

However, embodiments of the disclosure are not limited thereto. Many variations and/or modifications can be made to embodiments of the disclosure. In some other embodiments, the mark recess 108 is not formed.

Figure 1D:
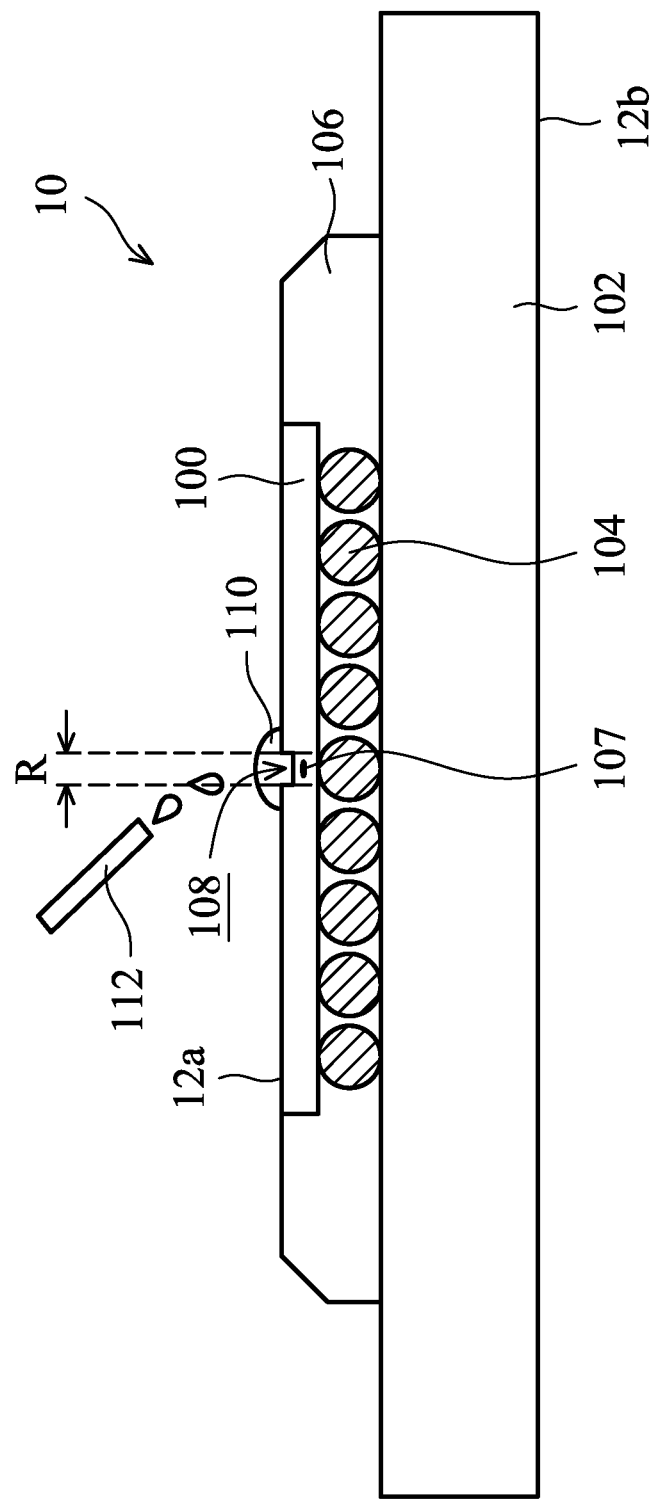

Afterwards, the method 200 continues with an operation S206 in which a polymer-containing solution (or a light curable glue) is dispensed over the target region, as shown in FIG. 2 in accordance with some embodiments. As shown in FIG. 1D, one or more droplets of a polymer-containing solution 110 is dispended or applied over the first surface 12a of the chip package 10, in accordance with some embodiments.

In some embodiments, it is not needed to apply the polymer-containing solution 110 on the entire surface 12a of the chip package 10. In some embodiments, the polymer-containing solution 110 is dispensed over the target region R using a solution provider 112. The solution provider 112 may include a syringe used to dispense the polymer-containing solution 110. In some embodiments, the polymer-containing solution 110 is dispensed directly on the mark recess 108 to fill the mark recess 108. The polymer-containing solution 110 may completely fill the mark recess 108.

In some embodiments, the polymer-containing solution 110 is a light curable glue. In some embodiments, the light curable glue includes or is made of an ultraviolet (UV) light curable epoxy resin. In some embodiments, the polymer-containing solution 110 is made of or includes one or more epoxy resins. In some embodiments, the polymer-containing solution 110 includes a mixture of epoxy resin and polyol. In some embodiments, the polymer-containing solution 110 further includes one or more other suitable diluents. In some embodiments, the polymer-containing solution 110 further includes one or more suitable photo initiators.

In some embodiments, the composition of the polymer-containing solution 110 is adjusted such that the polymer-containing solution 110 has a low viscosity, which may facilitate subsequent inspecting processes. The viscosity of the polymer-containing solution 110 may be in a range from about 115 cps to about 350 cps. In some embodiments, due to the low viscosity of the polymer-containing solution 110, the polymer-containing solution 110 completely fills the mark recess 108.

Figure 1E:
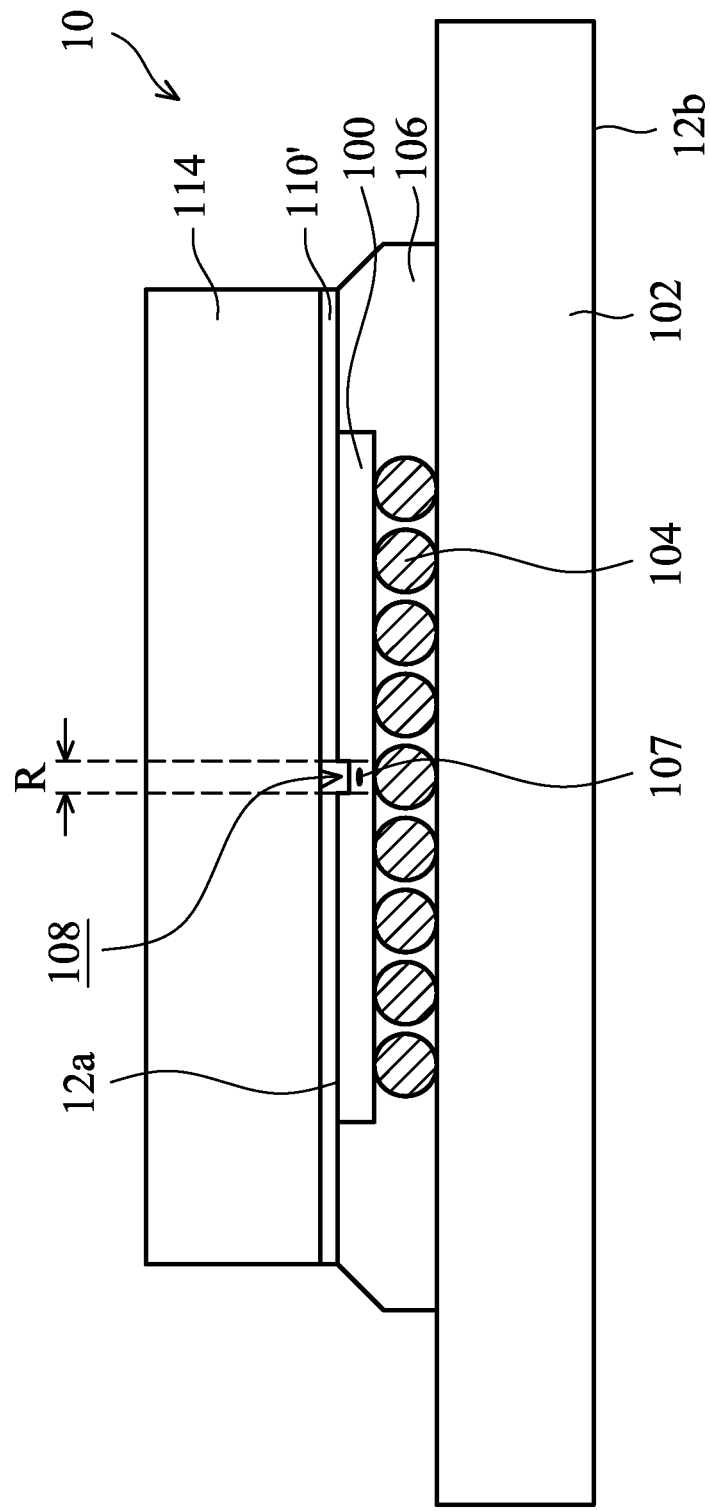

Afterwards, the method 200 continues with an operation S208 in which a carrier substrate is disposed over the semiconductor device structure, as shown in FIG. 2 in accordance with some embodiments. As shown in FIG. 1E, a carrier substrate 114 is disposed over the first surface 12a of the chip package 10 and the polymer-containing solution 110, in accordance with some embodiments.

In some embodiments, after disposing the carrier substrate 114, the polymer-containing solution 110 is pressed by the carrier substrate 114 and spreads between the carrier substrate 114 and the chip package 10. Due to the capillary effect of the polymer-containing solution 110 with low viscosity, the polymer-containing solution 110 may distribute evenly at the interface between the carrier substrate 114 and the chip package 10. In FIG. 1E, the reference number 110' is used to designate the spread or extended polymer-containing solution (or polymer-containing gel layer). The polymer-containing solution 110' may be confined between the carrier substrate 114 and the chip package 10.

In some embodiments, only a few amount of polymer-containing solution is required. The relative cost is therefore reduced. The subsequent cleaning operation may also be prevented or reduced since less glue is used. Lower fabrication cost and time may be achieved.

In some embodiments, the carrier substrate 114 is a transparent substrate. The carrier substrate 114 may include a glass substrate, a quartz substrate, a sapphire substrate, another suitable transparent substrate, or a combination thereof. In some embodiments, the carrier substrate 114 is made of a material which has high UV light transmittance. In some embodiments, the carrier substrate 114 also has a high visible light transmittance. The carrier substrate 114 may have a thickness that is in a range from about 250 µm to about 750 µm.

Figure 1F:
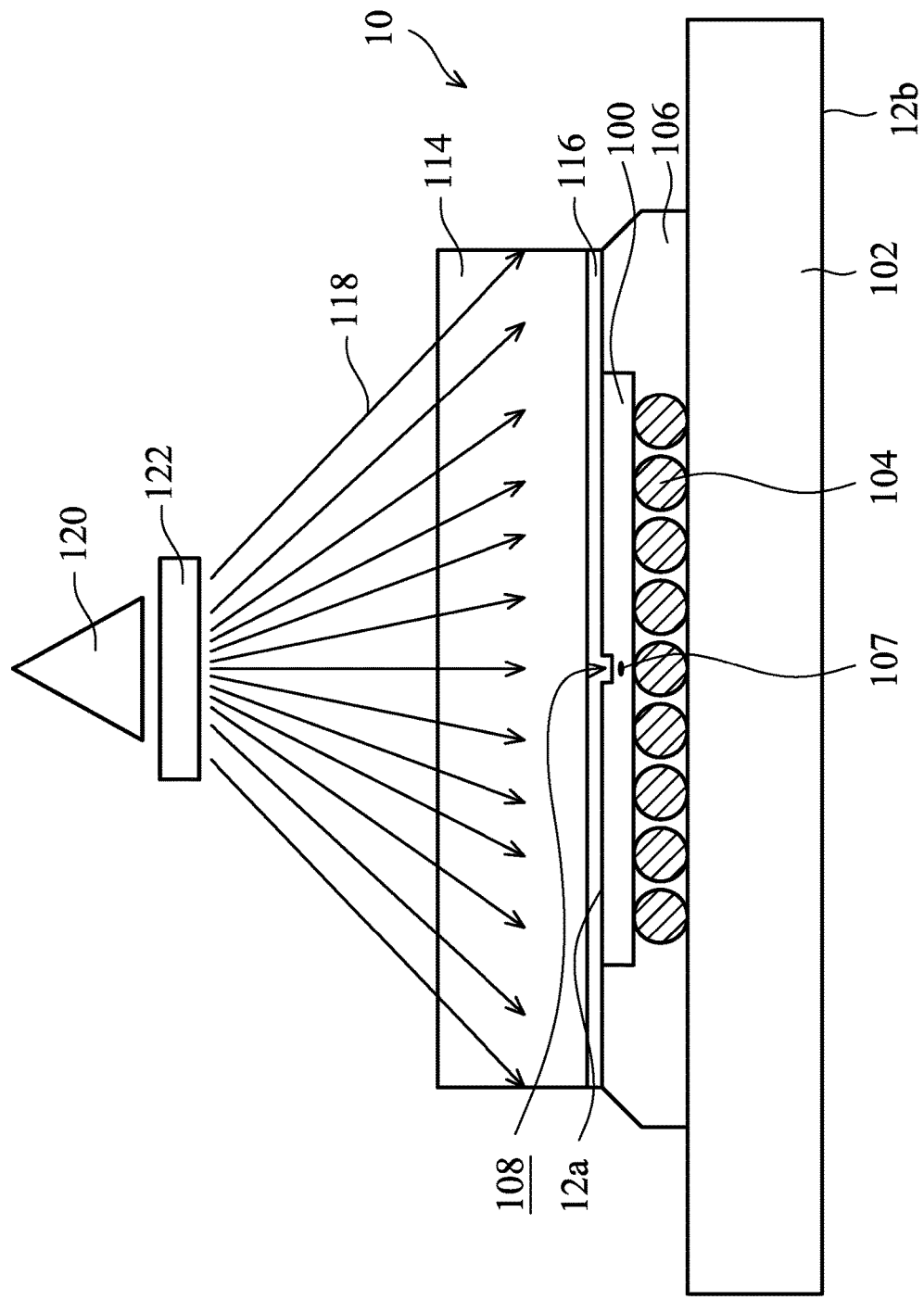

Afterwards, the method 200 continues with an operation S210 in which the polymer-containing solution is irradiated with a light to cure the polymer-containing solution, as shown in FIG. 2 in accordance with some embodiments. As shown in FIG. 1F, the polymer-containing solution 110' is irradiated with a light 118 provided by a light source 120, in accordance with some embodiments. The polymer-containing solution 110' is cured by the light 118 and is transformed to form an adhesive layer 116. Adhesion of the adhesive layer 116 is higher than that of the polymer-containing solution 110'.

The adhesive layer 116 may be cured UV glue or cured UV epoxy resin. After being cured by the light 118, cross-linking reactions may occur in the polymer-containing solution 110' to form the adhesive layer 116 that bonds the carrier substrate 114 and the chip package 10. Therefore, due to strong bonding between the carrier substrate 114 and the chip package 10, the carrier substrate 114 may be used to hold and support the thinned chip package 10 during subsequent inspecting processes.

In some embodiments, before being irradiated with the light 118, the polymer-containing solution (or polymer-containing gel layer) 110' confined between the carrier substrate 114 and the chip package 10 has a thickness that is in a range from about 5 µm to about 20 µm. After being cured by the light 118, the formed adhesive layer 116 may slightly shrink when compared with the polymer-containing solution (or polymer-containing gel layer) 110'. The adhesive layer 116 may have a thickness that is in a range from about 1 µm to about 19 µm. In some other embodiments, the adhesive layer 116 does not substantially shrink when compared with the polymer-containing solution (or polymer-containing gel layer) 110'.

In some embodiments, the light 118 is capable of transforming the polymer-containing solution 110' into the adhesive layer 116. In some embodiments, the light 118 includes UV light. The light 118 may include radiation of different wavelengths. The wavelengths of the light 118 may be in a range from about 300 nm to about 400 nm. However, embodiments of the disclosure are not limited thereto. Many variations and/or modifications can be made to embodiments of the disclosure. In some other embodiments, the light 118 has a different wavelength range. In some embodiments, the intensity of the light 118 is in a range from about 10 mW/cm$^2$ to about 100 mW/cm$^2$. In some embodiments, the irradiation time of the light 118 is in a range from about 1 second to about 10 seconds.

Since the adhesive layer 114 is formed by light irradiation but not by thermal curing, there is substantially no thermal load or thermal stress on the chip package 10. Problems caused due to different thermal expansion coefficients of different materials may be prevented. Cracking of the semiconductor die 100 is prevented since substantially no thermal impact is applied on the semiconductor die 100. Delamination between the semiconductor die 100 and the underfill layer 106 is also prevented. Since cracking and delamination issues are prevented, the to-be-inspected feature 107 may be maintained in a better condition without being damaged.

In some other cases, a thermal operation may be used to bond the carrier substrate with the to-be-inspected structure. The thermal operation may cause high thermal stress on the to-be-inspected structure, which may lead to cracking and/or delamination. The to-be-inspected feature therein may be damaged or destroyed, which negatively affects the defect analysis or debug operation.

As shown in FIG. 1F, a filter element 122 is used to filter out infrared (IR) light and visible light generated from the light source 120, in accordance with some embodiments. Due to the filter element 112, the light reaching the polymer-containing solution (or polymer-containing gel layer) 110' is limited within a specific wavelength range. As a result, the polymer-containing solution (or polymer-containing gel layer) 110' and the chip package 10 are prevented from being heated during the light curing operation for forming the adhesive layer 116. Therefore, cracking and/or delamination of the chip package 10 caused by thermal operation are prevented. The to-be-inspected feature 107 may be maintained in a better condition for subsequent inspecting processes.

In some embodiments, the adhesive layer 116 and the carrier substrate 114 are visibly transparent. Therefore, the mark recess 108 indicating the target region R is still visible, which facilitates subsequent inspecting processes. It is not needed to take a lot of time for alignment.

Afterwards, the method 200 continues with an operation S212 in which the to-be-inspected feature is inspected, as shown in FIG. 2 in accordance with some embodiments.

Figure 1G:
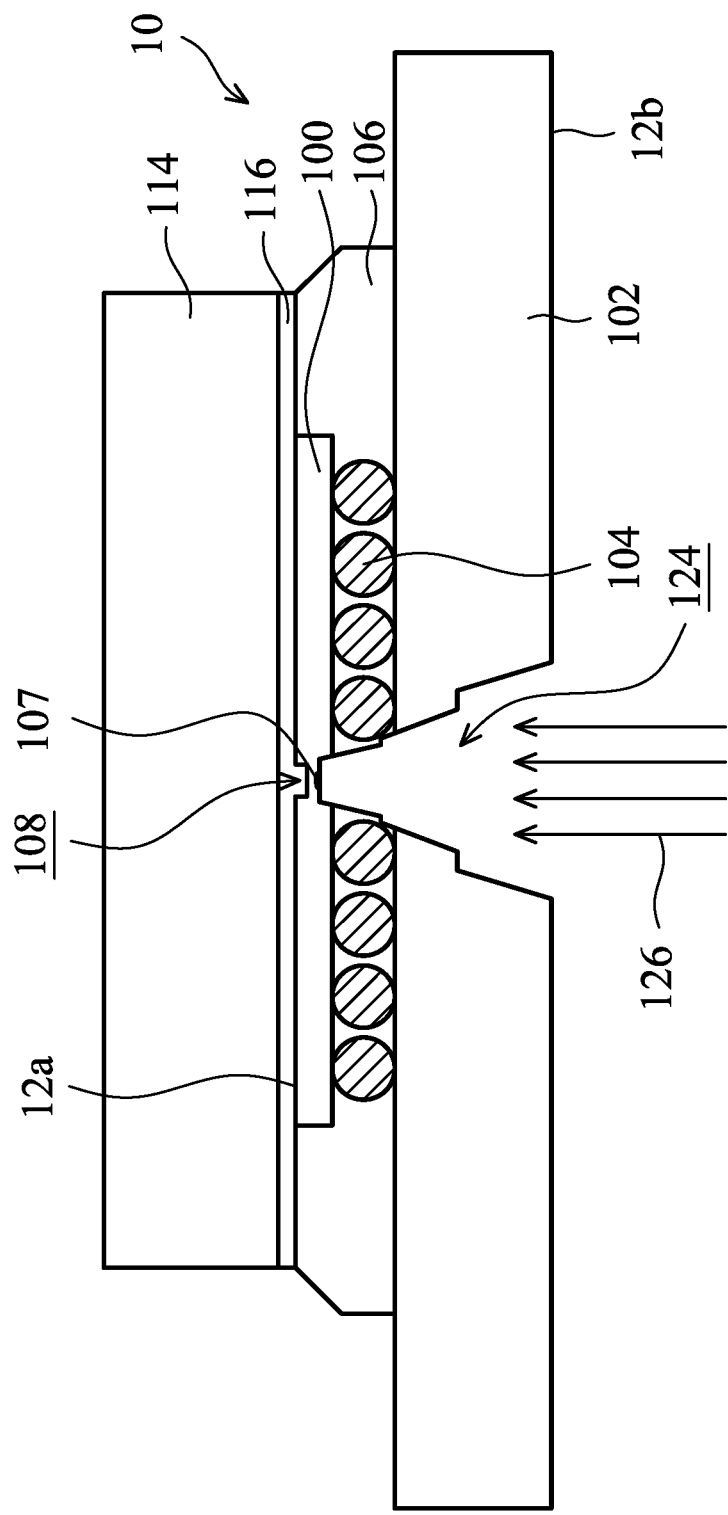

As shown in FIG. 1G, before inspecting the to-be-inspected feature 107, the chip package 10 is partially removed from the second surface 12b to form an opening 124, in accordance with some embodiments. The opening 124 extends towards the to-be-inspected feature 107. In some embodiments, the opening 124 exposes the to-be-inspected feature 107. In some other embodiments, the opening 124 is about to expose the to-be-inspected feature 107. In these cases, the to-be-inspected feature 107 can still be inspected or observed. For example, a scanning electron microscope may be used to inspect the to-be-inspected feature 107.

In some embodiments, the to-be-inspected feature 107 is inspected after the formation of the opening 124. In some other embodiments, the to-be-inspected feature 107 is inspected during the formation of the opening 124. In some embodiments, the formation of the opening 124 and the inspecting of the to-be-inspected feature 107 are simultaneously performed. Once the to-be-inspected feature 107 can be inspected clearly, the formation of the opening 124 is terminated.

In some embodiments, the opening 124 is formed using an energy beam 126, as shown in FIG. 1G. The energy beam 126 may include an ion beam, an electron beam, a laser beam, a plasma beam, one or more other suitable energy beams, or a combination thereof.

However, embodiments of the disclosure are not limited thereto. Many variations and/or modifications can be made to embodiments of the disclosure. In some other embodiments, the opening 124 is formed using a mechanical drilling process. In some embodiments, the opening 124 is formed using a combination of a mechanical drilling process and an energy beam drilling process. For example, a mechanical drilling process may be used first. Afterwards, an energy beam drilling process is used to further recess the opening 124.

Figure 3:
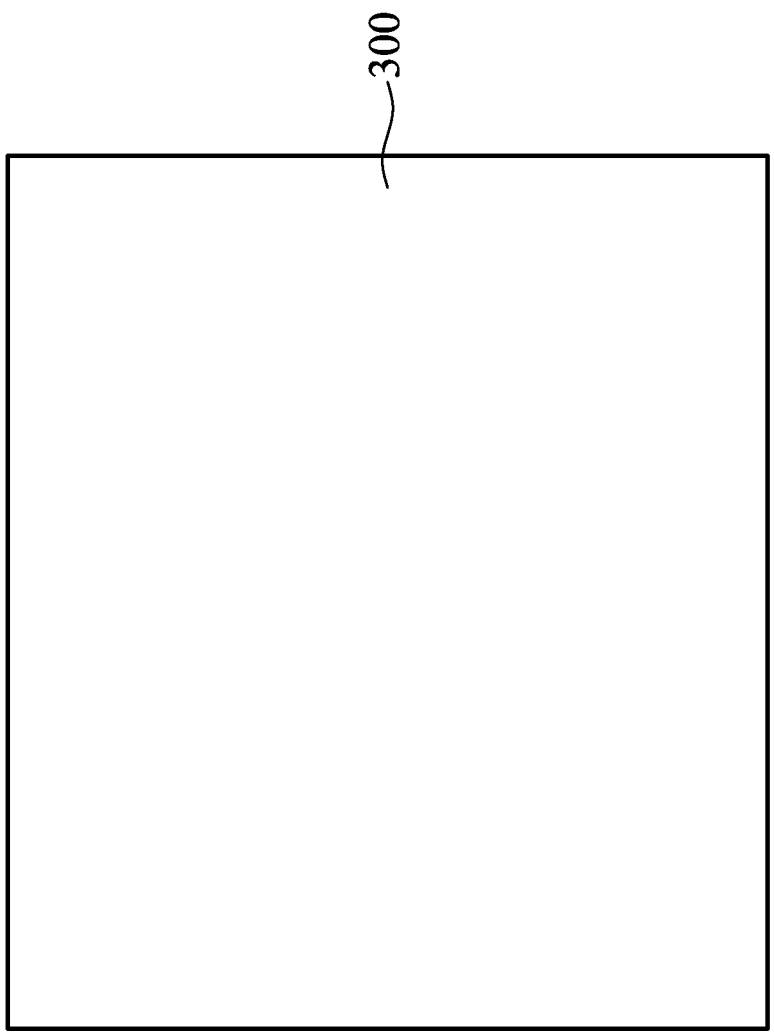
FIG. 3 is a cross-sectional view of a vacuum chamber used for inspecting a semiconductor device structure, in accordance with some embodiments.

In some embodiments, the to-be-inspected feature 107 is inspected or observed using an electron microscope. FIG. 3 is a cross-sectional view of a vacuum chamber 300 used for inspecting a semiconductor device structure, in accordance with some embodiments. In some embodiments, the vacuum chamber 300 is a portion of an electron microscope. The electron microscope may be a scanning electron microscope (SEM).

In some embodiments, after the formation of the adhesive layer 116, the structure shown in FIG. 1F is transferred into the vacuum chamber 300 of an electron microscope. As shown in FIGS. 1G and 3, the subsequent formation of the opening 124 and the inspecting of the to-be-inspected feature 107 are performed in the vacuum chamber 300, in accordance with some embodiments. In some embodiments, the chip package 10 is partially removed layer by layer using the energy beam 126 during the formation of the opening 124. The energy beam 126 may be an ion beam which is generated from an ion beam gun of the electron microscope. The energy beam 126 may be used to continuously further recess the opening 124 until the to-be-inspected feature 107 is observed or inspected using the electron microscope. The to-be-inspected feature 107 may be inspected during or after the formation of the opening 124.

In some embodiments mentioned above, the semiconductor device structure that is inspected is a chip package. However, embodiments of the disclosure are not limited thereto. Many variations and/or modifications can be made to embodiments of the disclosure. In some other embodiments, the semiconductor device structure to be inspected includes a semiconductor chip, a semiconductor wafer, or another suitable structure.

Figure 4A:
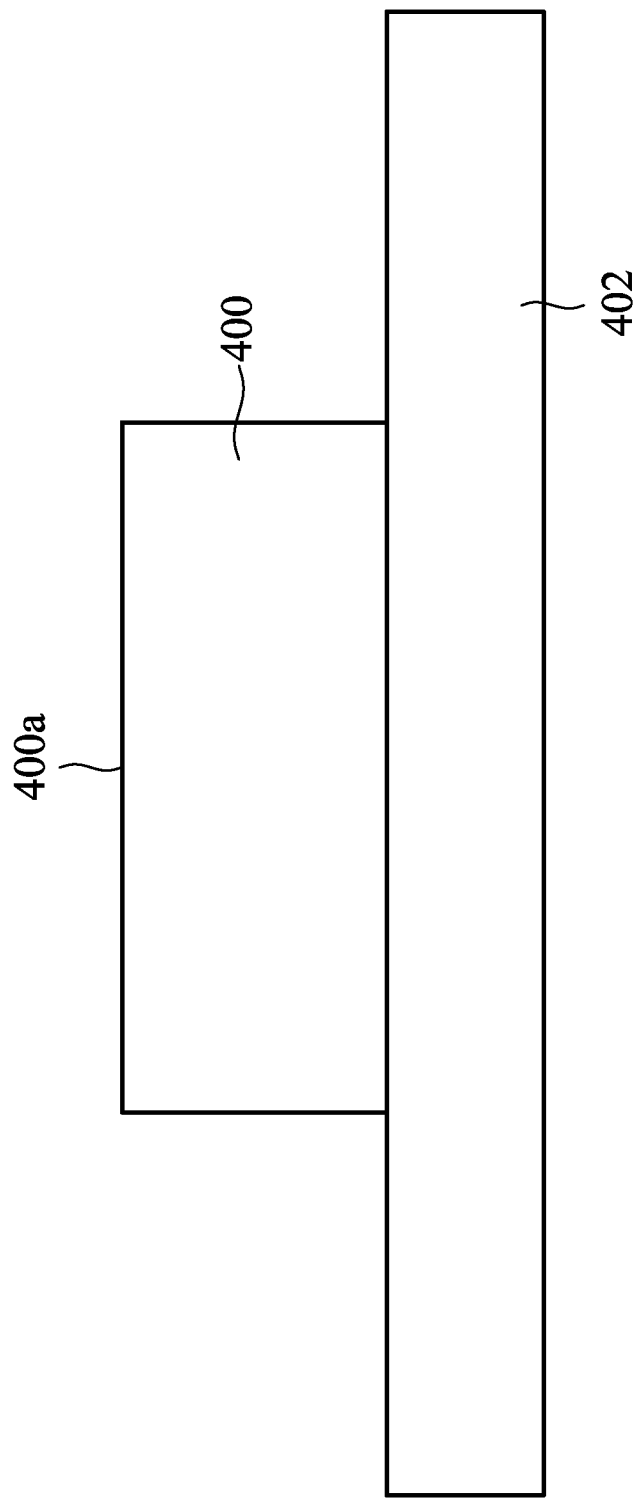
FIGS. 4A-4G are cross-sectional views of various stages of a process for inspecting a semiconductor device structure, in accordance with some embodiments.

FIGS. 4A-4G are cross-sectional views of various stages of a process for inspecting a semiconductor device structure, in accordance with some embodiments. As shown in FIG. 4A, a semiconductor device structure 400 is received. The semiconductor device structure 400 may be a semiconductor chip, a semiconductor wafer, a chip package, or a wafer package. As shown in FIG. 4A, the semiconductor device structure 400 has a surface 400a. In some embodiments, the surface 400a is a back side surface of the semiconductor device structure. In some embodiments, the semiconductor device structure 400 is bonded on a support substrate 402. The support substrate 402 may be made of or include a semiconductor material, a polymer material, a dielectric material, one or more other suitable materials, or a combination thereof.

Figure 4B:
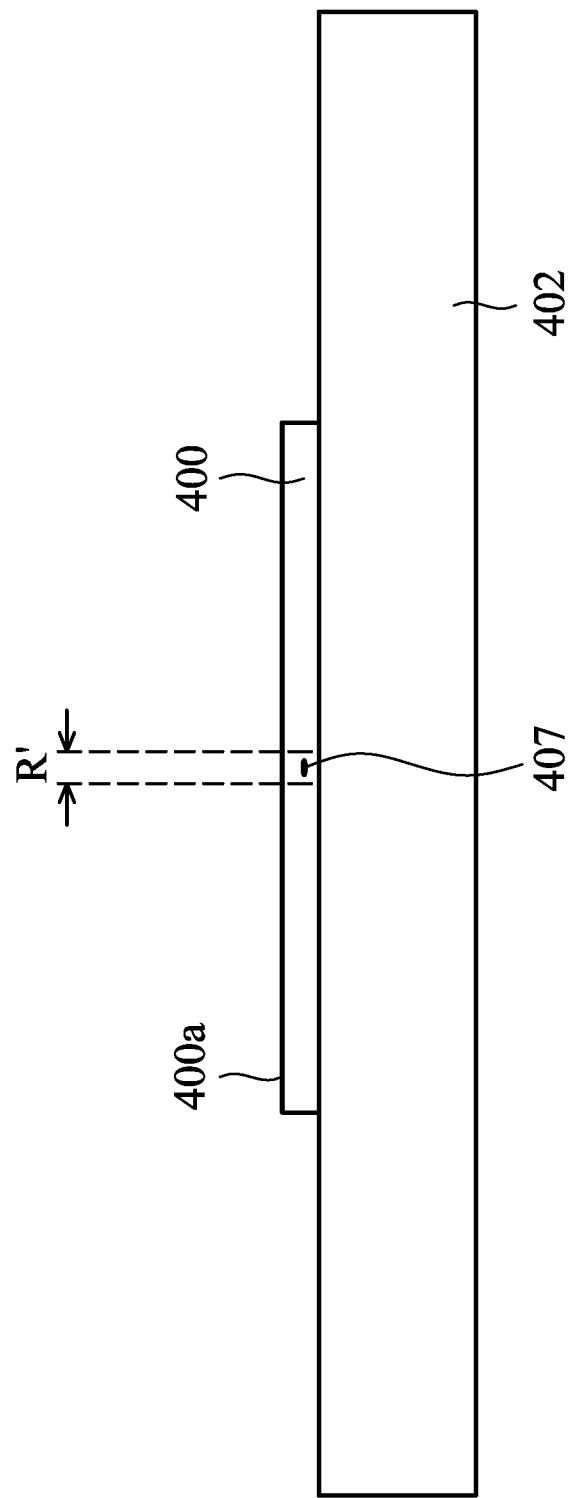

As shown in FIG. 4B, the semiconductor device structure 400 is thinned, in accordance with some embodiments. Afterwards, processes and/or operations similar to those illustrated in FIG. 1B are performed to identify a target region R' which contains a to-be-inspected feature 407.

Figure 4C:
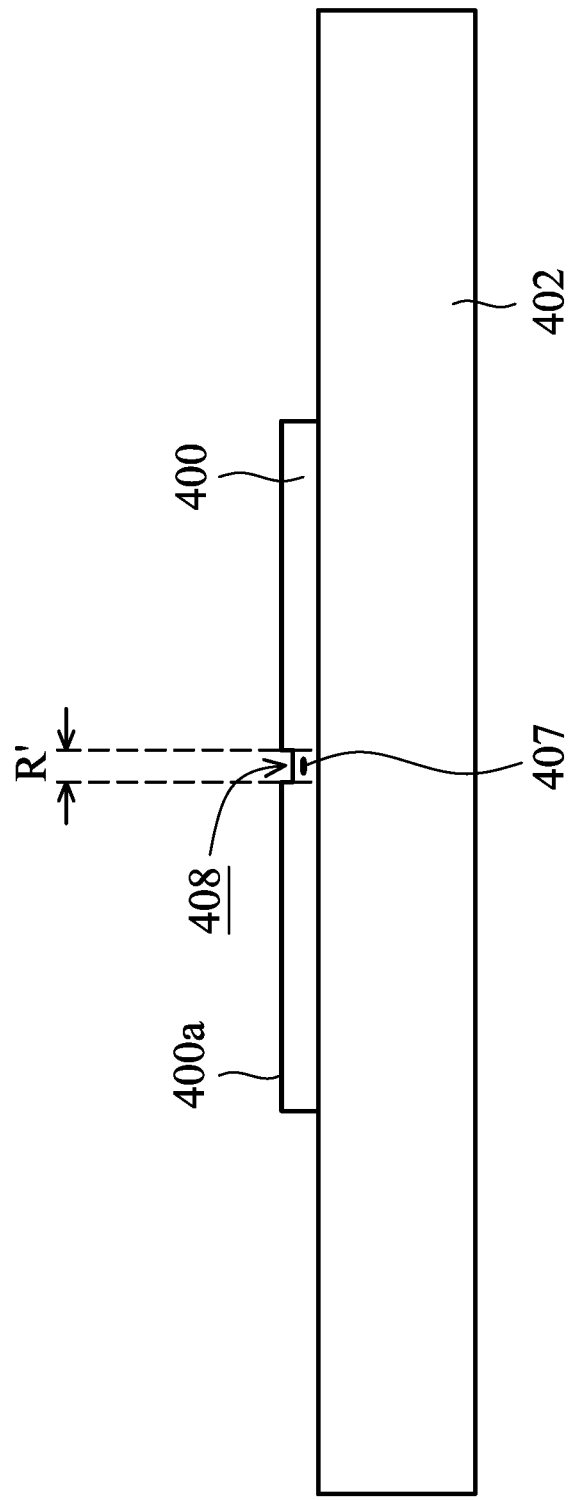

As shown in FIG. 4C, a mark recess 408 that extends towards the to-be-inspected feature 407 is formed, in accordance with some embodiments. In some embodiments, the process used for forming the mark recess 108 in FIG. 1C is used to form the mark recess 408. The mark recess 408 may be used to label the area where the to-be-inspected feature 407 is positioned.

Figure 4D:
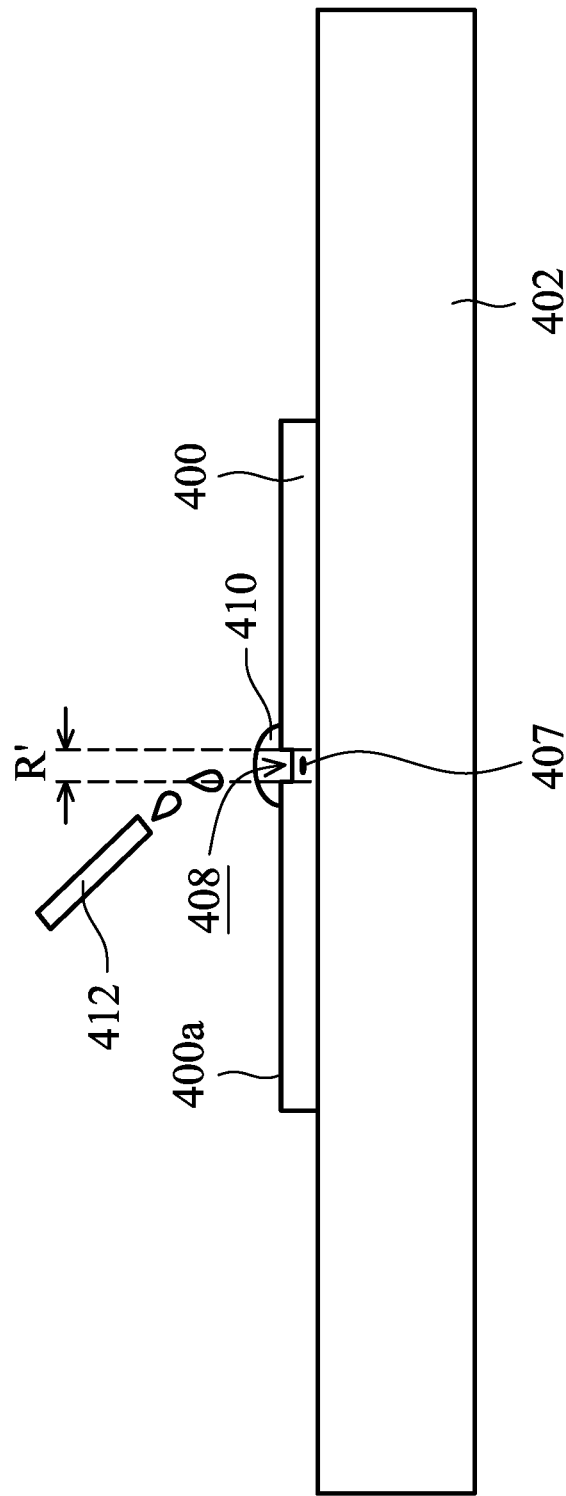

As shown in FIG. 4D, a light curable glue 410 is dispensed or applied on the mark recess 408, in accordance with some embodiments. The light curable glue 410 may be dispensed or applied using a glue provider 412. In some embodiments, the material of the light curable glue 410 is the same as or similar to that of the polymer-containing solution 110.

Figure 4E:
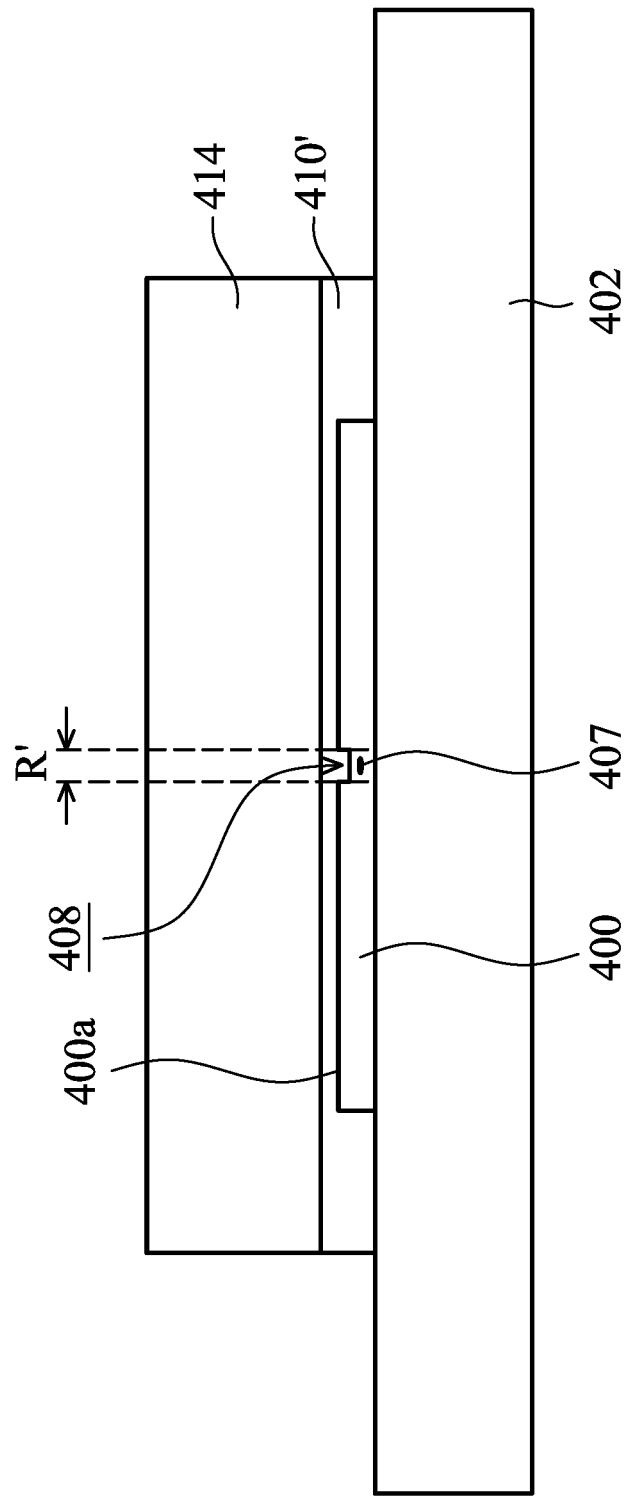

As shown in FIG. 4E, a carrier substrate 414 is disposed over the semiconductor device structure 100, in accordance with some embodiments. In some embodiments, the light curable glue 410 has a low viscosity. Therefore, the light curable glue 410 may be pressed by the carrier substrate 414 and then extend between the carrier substrate 414 and the semiconductor device structure 400. As shown in FIG. 4E, an extended light curable glue layer 410' is formed between the carrier substrate 402 and the semiconductor device structure 400.

Figure 4F:
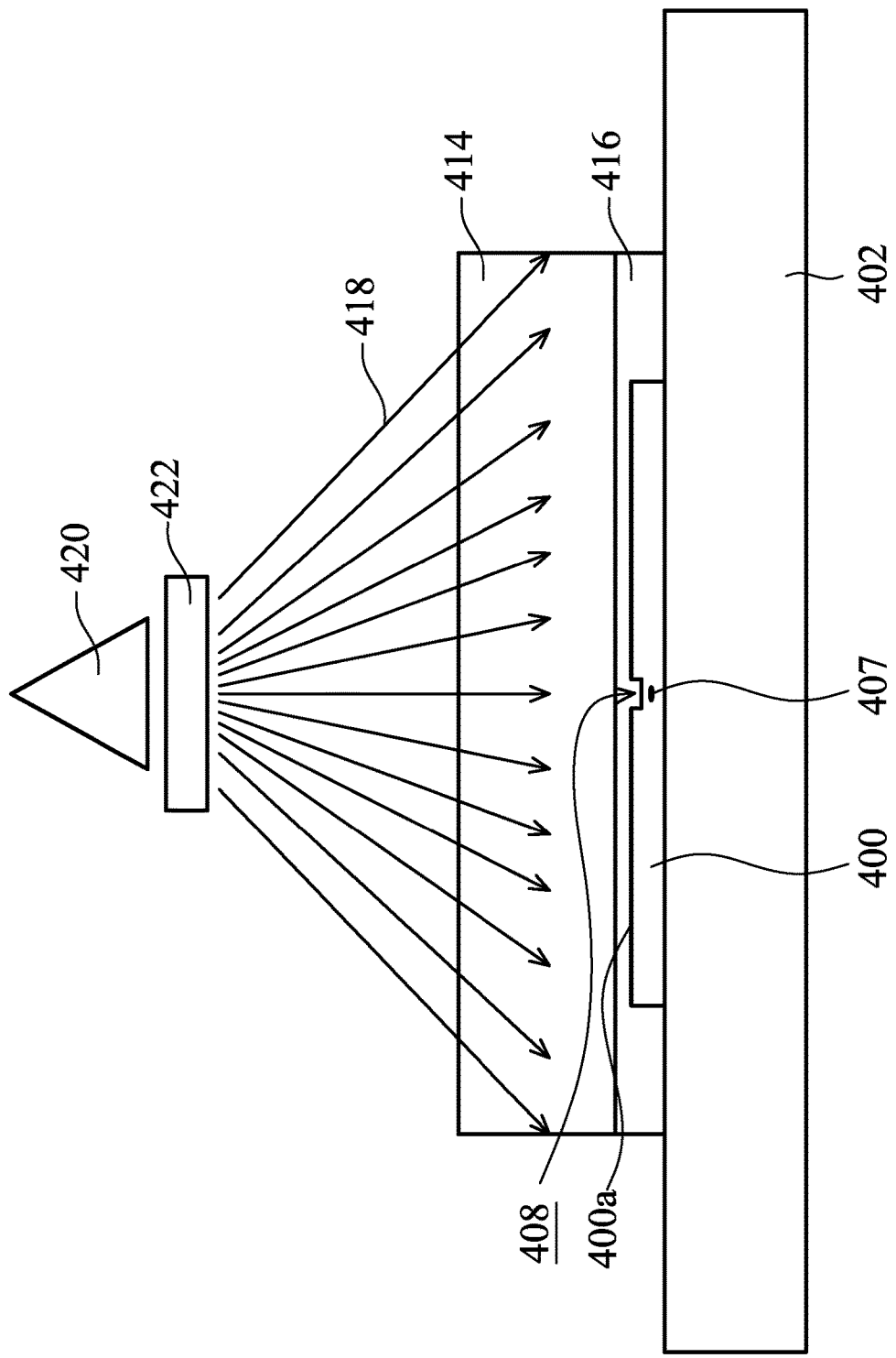

As shown in FIG. 4F, the light curable glue 410 is cured with a light 418 to become an adhesive layer 416 that bonds the carrier substrate 414 and the semiconductor device structure 400. A light source 420 may be used to provide the light 418. A filter element 422 may be used to filter out light with unsuitable wavelengths. In some embodiments, the light 418 applied on the light curable glue 410 is a UV light.

Figure 4G:
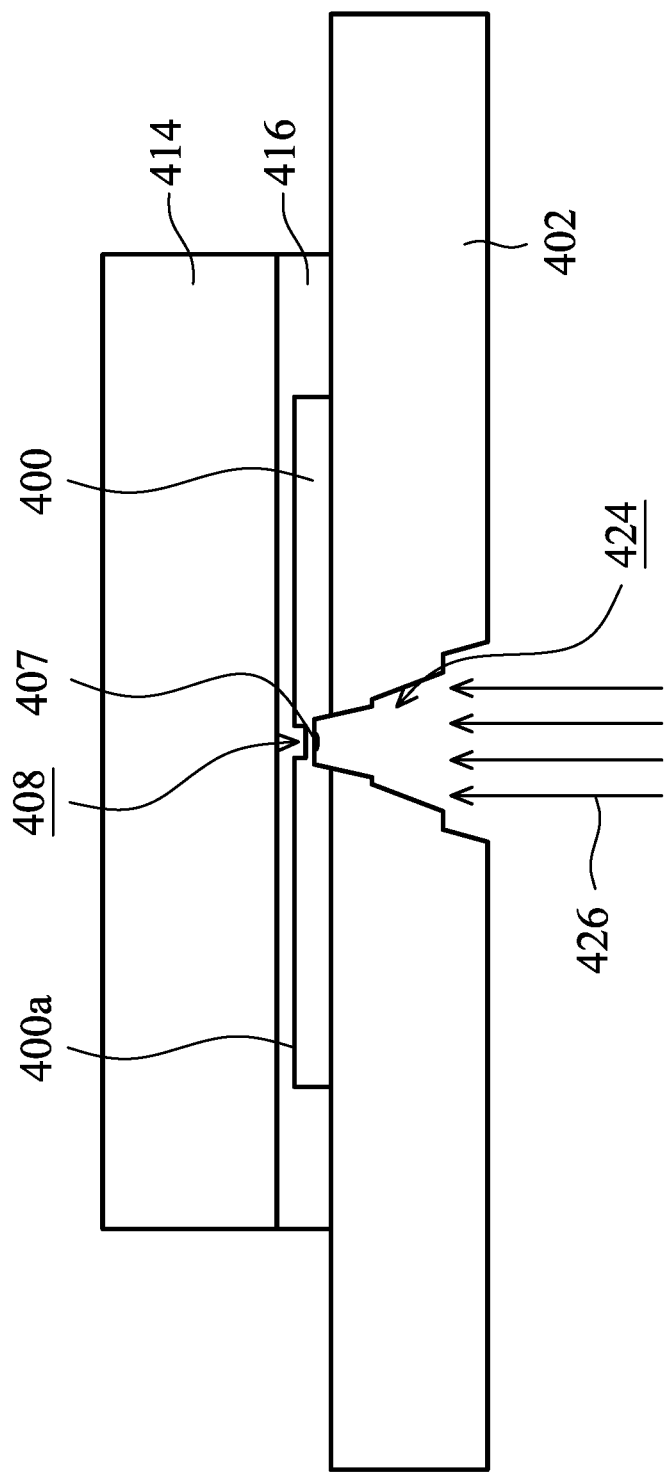

As shown in FIG. 4G, an energy beam 426 is used to partially remove the support substrate 402 and the semiconductor device structure 400, in accordance with some embodiments. An opening 424 is therefore formed, as shown in FIG. 4G. The mark recess 408 functions as an alignment target for the energy beam drilling process. The opening 424 extends towards the to-be-inspected feature 407.

In some embodiments, the operations illustrated in FIG. 4G are performed in a vacuum chamber of a scanning electron microscope. In some embodiments, the energy beam 426 (such as an ion beam) is directed to form the opening 424 substantially aligned with the mark recess 408. The semiconductor device structure 400 may be removed layer by layer during the drilling of the energy beam 426. The image of the bottom of the opening 424 is also observed during the formation of the opening 424. The energy beam 426 may be used to continuously partially remove the semiconductor device structure 400 until the to-be-inspected feature 407 is exposed or detectable.

In some embodiments, the to-be-inspected feature 407 is a yield-limiting defect, a design-functional defect and/or a performance-limiting defect. Processing issues may be identified by inspecting the to-be-inspected feature 407. The process flow may be adjusted or modified accordingly. The performance and quality of the semiconductor device structure may therefore be improved.

Embodiments of the disclosure use a light curable glue (or a polymer-containing solution) to assist in inspecting a semiconductor device structure. The light curable glue is used to achieve a bonding between a carrier substrate and a semiconductor device structure containing a specific feature which is intended to be inspected. UV light may be used to cure the light curable glue for forming an adhesive layer bonding the carrier substrate and the semiconductor device structure. Therefore, subsequent inspection operations may be performed to inspect the specific feature in the semiconductor device structure. Since the semiconductor device structure is not heated during the inspection operations, thermal stress is prevented. Cracking and/or delamination of the semiconductor device structure are prevented. The specific feature may be maintained in a better condition for the subsequent inspection operations.

In accordance with some embodiments, a method for inspecting a semiconductor device structure is provided. The method includes receiving a semiconductor device structure having a to-be-inspected feature. The semiconductor device structure has a first surface and a second surface. The method also includes applying a polymer-containing solution over the first surface of the semiconductor device structure. The method further includes disposing a transparent substrate over the first surface of the semiconductor device structure and the polymer-containing solution. In addition, the method includes irradiating the polymer-containing solution with a light to form an adhesive layer between the transparent substrate and the semiconductor device structure. The adhesive layer bonds the transparent substrate and the semiconductor device structure. The method also includes inspecting the to-be-inspected feature.

In accordance with some embodiments, a method for inspecting a semiconductor device structure is provided. The method includes receiving a chip package having a to-be-inspected feature, and the chip package has a first surface and a second surface. The method also includes applying a polymer-containing solution over the first surface of the chip package. The method further includes disposing a carrier substrate over the first surface of the chip package such that the polymer-containing solution spreads between the carrier substrate and the chip package. In addition, the method includes irradiating the polymer-containing solution with a light to transform the polymer-containing solution into an adhesive layer bonding the carrier substrate and the chip package. The method also includes partially removing the chip package from the second surface to form an opening extending towards the to-be-inspected feature. The method further includes inspecting the to-be-inspected feature after or during the formation of the opening.

In accordance with some embodiments, a method for inspecting a semiconductor device structure is provided. The method includes receiving a semiconductor device structure having a to-be-inspected feature, and the semiconductor device structure has a first surface and a second surface. The method also includes identifying a target region of the semiconductor device structure, and the to-be-inspected feature is in the target region. The method further includes dispensing one or more droplets of a polymer-containing solution over the target region. In addition, the method includes disposing a transparent substrate over the semiconductor device structure such that the polymer-containing solution spreads between the transparent substrate and the chip package. The method includes irradiating the polymer-containing solution with an ultraviolet light to cure the polymer-containing solution such that an adhesive layer bonding the transparent substrate and the semiconductor device structure is formed. The method also includes forming an opening extending from the second surface of the semiconductor device structure towards the to-be-inspected feature. The method further includes inspecting the to-be-inspected feature after or during the formation of the opening.

The foregoing outlines features of several embodiments such that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for inspecting a semiconductor device structure, comprising:
   receiving a semiconductor device structure comprising a to-be-inspected feature, wherein the semiconductor device structure has a first surface and a second surface;
   applying a polymer-containing solution over the first surface of the semiconductor device structure;
   disposing a transparent substrate over the first surface of the semiconductor device structure and the polymer-containing solution;
   irradiating the polymer-containing solution with a light to form an adhesive layer between the transparent substrate and the semiconductor device structure, wherein the adhesive layer bonds the transparent substrate and the semiconductor device structure; and
   inspecting the to-be-inspected feature.

2. The method for inspecting a semiconductor device structure as claimed in claim 1, further comprising partially removing the semiconductor device structure from the second surface to form an opening extending towards the to-be-inspected feature, wherein the to-be-inspected feature is inspected after or during the formation of the opening.

3. The method for inspecting a semiconductor device structure as claimed in claim 2, wherein the opening is formed using an energy beam.

4. The method for inspecting a semiconductor device structure as claimed in claim 2, wherein the opening is formed using a mechanical drilling process.

5. The method for inspecting a semiconductor device structure as claimed in claim 1, wherein the polymer-containing solution comprises an ultraviolet light curable epoxy resin.

6. The method for inspecting a semiconductor device structure as claimed in claim 1, wherein the light has a wavelength, and the wavelength is in a range from about 300 nm to about 400 nm.

7. The method for inspecting a semiconductor device structure as claimed in claim 6, further comprising using a filter element to filter out infrared light and visible light while irradiating the polymer-containing solution with the light.

8. The method for inspecting a semiconductor device structure as claimed in claim 1, further comprising thinning the semiconductor device structure from the first surface before applying the polymer-containing solution.

9. The method for inspecting a semiconductor device structure as claimed in claim 8, further comprising:
   inspecting the semiconductor device structure after thinning the semiconductor device structure to locate a target region where the to-be-inspected feature is positioned; and
   thinning the target region before applying the polymer-containing solution.

10. The method for inspecting a semiconductor device structure as claimed in claim 9, wherein the polymer-containing solution is applied on the target region after the target region is thinned.

11. The method for inspecting a semiconductor device structure as claimed in claim 1, wherein the to-be-inspected feature is inspected using an electron microscope.

12. A method for inspecting a semiconductor device structure, comprising:
   receiving a chip package comprising a to-be-inspected feature, wherein the chip package has a first surface and a second surface;
   applying a polymer-containing solution over the first surface of the chip package;
   disposing a carrier substrate over the first surface of the chip package such that the polymer-containing solution spreads between the carrier substrate and the chip package;
   irradiating the polymer-containing solution with a light to transform the polymer-containing solution into an adhesive layer bonding the carrier substrate and the chip package;
   partially removing the chip package from the second surface to form an opening extending towards the to-be-inspected feature; and
   inspecting the to-be-inspected feature after or during the formation of the opening.

13. The method for inspecting a semiconductor device structure as claimed in claim 12, wherein the chip package is partially removed layer by layer using an energy beam during the formation of the opening until the to-be-inspected feature is observed by an electron microscope.

14. The method for inspecting a semiconductor device structure as claimed in claim 12, further comprising thinning the chip package from the first surface before applying the polymer-containing solution.

15. The method for inspecting a semiconductor device structure as claimed in claim 14, further comprising:
   inspecting the chip package after thinning the chip package to locate a target region where the to-be-inspected feature is positioned; and
   marking the target region before applying the polymer-containing solution.

16. The method for inspecting a semiconductor device structure as claimed in claim 14, wherein a semiconductor die of the chip package is thinned during the thinning of the chip package, and the to-be-inspected feature is positioned in the semiconductor die.

17. A method for inspecting a semiconductor device structure, comprising:
   receiving a semiconductor device structure comprising a to-be-inspected feature, wherein the semiconductor device structure has a first surface and a second surface;
   identifying a target region of the semiconductor device structure, wherein the to-be-inspected feature is in the target region;
   dispensing one or more droplets of a polymer-containing solution over the target region;
   disposing a transparent substrate over the semiconductor device structure such that the polymer-containing solution spreads between the transparent substrate and the chip package;
   irradiating the polymer-containing solution with an ultraviolet light to cure the polymer-containing solution such that an adhesive layer bonding the transparent substrate and the semiconductor device structure is formed;
   forming an opening extending from the second surface of the semiconductor device structure towards the to-be-inspected feature; and
   inspecting the to-be-inspected feature after or during the formation of the opening.

18. The method for inspecting a semiconductor device structure as claimed in claim 17, further comprising thinning the semiconductor device structure before the target region is identified, wherein the target region is identified using an infrared light.

19. The method for inspecting a semiconductor device structure as claimed in claim 17, further comprising thinning the target region using a mechanical drilling process before applying the polymer-containing solution.

20. The method for inspecting a semiconductor device structure as claimed in claim 17, wherein the formation of the opening and the inspecting of the to-be-inspected feature are performed in a same vacuum chamber.

* * * * *